United States Patent [19]

Chang et al.

[11] Patent Number: 4,554,396
[45] Date of Patent: Nov. 19, 1985

[54] OLEFIN UPGRADING WITH FERROSILICATE ZEOLITE CATALYST

[75] Inventors: Clarence D. Chang, Princeton; Cynthia T. W. Chu, Pennington, both of N.J.

[73] Assignee: Mobil Oil Corporation, New York, N.Y.

[21] Appl. No.: 651,748

[22] Filed: Sep. 18, 1984

[51] Int. Cl.$^4$ ................................................ C07C 2/02
[52] U.S. Cl. ..................................... 585/531; 585/533
[58] Field of Search ............................... 585/531, 533

[56] References Cited

U.S. PATENT DOCUMENTS

| | | | |
|---|---|---|---|
| 4,100,218 | 7/1978 | Chen et al. | 260/673 |
| 4,208,305 | 6/1980 | Kouwenhoven et al. | 252/431 |
| 4,238,318 | 12/1980 | Kouwenhoven et al. | 208/120 |
| 4,244,807 | 1/1981 | Dautzenberg et al. | 208/66 |
| 4,324,940 | 4/1982 | Dessau | 585/466 |
| 4,417,088 | 11/1983 | Miller | 585/533 |
| 4,420,467 | 12/1983 | Whittam | 423/326 |
| 4,423,269 | 12/1983 | Miller | 585/533 |

Primary Examiner—Curtis R. Davis
Attorney, Agent, or Firm—Alexander J. McKillop; Michael G. Gilman; L. G. Wise

[57] ABSTRACT

A process for upgrading lower olefin to produce heavier hydrocarbons having a substantially linear molecular conformation comprising contacting olefinic feedstock under oligomerization conditions at reaction temperature and pressure favorable to formation of higher molecular weight aliphatic hydrocarbons with a shape selective medium pore acidic crystalline ferrosilicate zeolite catalyst having a major portion of zeolitic iron in tetrahedral coordination therein.

8 Claims, No Drawings

OLEFIN UPGRADING WITH FERROSILICATE ZEOLITE CATALYST

BACKGROUND OF THE INVENTION

This invention relates to a novel catalytic process for converting olefins to heavier hydrocarbons.

Shape-selective oligomerization, as it applies to the conversion of $C_2$–$C_{10}$ olefins over aluminosilicate ZSM-5, is known to produce higher olefins up to $C_{30}$ and higher. As reported by Garwood in Preprints, Div. Petrol. Chem., ACS, 27(2), 563(1983), reaction conditions favoring higher molecular weight product are low temperature (200°–260° C.), high pressure (300–1500 psig), and long contact time (0.5–1 WHSV). The reaction under these conditions proceeds through the acid-catalyzed steps of (1) oligomerization, (2) isomerization-cracking to a mixture of intermediate carbon number olefins, and (3) copolymerization to give a continuous boiling product containing all carbon numbers. The channel systems of ZSM-5 type zeolite catalysts impose shape-selective constraints on the configuration of the large molecules, accounting for significant differences with other catalysts.

The following model reaction path for propene is set forth for purposes of explanation, and it should be taken as a theoretical path, as the process is presently understood by workers in the field.

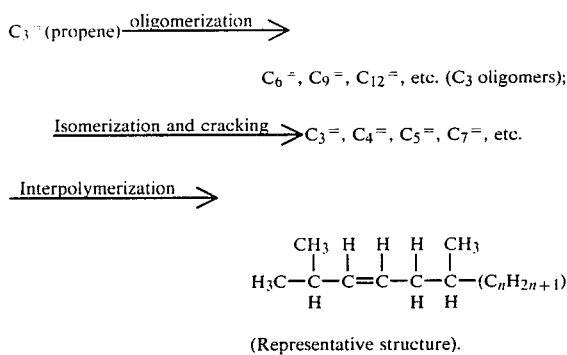

(Representative structure).

The desired oligomerization-polymerization products are substantially linear aliphatic hydrocarbons. The ZSM-5 catalytic path for propene feed provides a long chain with one methyl substituent per 4–5 carbon atoms in the straight chain. There are four distinct reactions occurring. First, propene will oligomerize to distinct $C_6$, $C_9$, $C_{12}$, etc. oligomers. These then isomerize and recrack, forming a range of light olefins. These intermediates then repolymerize to an equilibrium (or pseudo-equilibrium) distribution of heavier iso-olefin. As a result of having both forward (polymerization) and reverse (cracking), a continuous molecular weight distribution will occur in the product which can be independent of the carbon number of the starting olefin. For example, Garwood has previously shown, at constant temperature and pressure, virtually identical product distribution for feedstocks of ethene ($C_2^=$), propene ($C_3^=$), pentene ($C_5^=$), hexene ($C_6^=$), and decene ($C_{10}^=$). Structurally the final product is influenced by the pore structure of the catalyst. For low carbon number products (i.e., $C_4$, $C_5$) isomer distribution is approximately at equilibrium. For the higher carbon numbers, the structure is primarily a methyl-branched straight olefinic chain, with the maximum cross section of the chain limited by the dimension of the largest ZSM-5 pore. At conditions chosen to maximize heavy distillate range products ($C_{10}^+$) the raw aliphatic product is essentially mono-olefinic, with 10% or less of the double bond in the alpha position. Overall branching is not extensive, with most branches being methyl.

SUMMARY OF THE INVENTION

A new catalytic process has been discovered for upgrading lower olefins by oligomerization/polymerization reactions employing a medium-pore pentasil ferrosilicate zeolite. It has been found that certain ferrosilicates have superior catalytic activity in the conversion of lower olefins to liquid hydrocarbons, useful in the production of gasoline, distillate and lubricant materials. It is believed that those ferrosilicates of the pentasil type having a high proportion of tetrahedrally bound iron are particularly active in the oligomerization/polymerization reactions.

In the preferred embodiments the feedstock comprises a major portion of $C_3$–$C_4$ olefin and the conversion is conducted at elevated temperature and pressure at relatively low space velocity to favor production of $C_6^+$ gasoline, $C_{10}^+$ distillate and $C_{20}^+$ lubricant oils.

DESCRIPTION OF THE PREFERRED EMBODIMENTS

The oligomerization/polymerization catalysts preferred for use herein include the crystalline ferrosilicate zeolites having a constraint index of about 1 to 12, representative of the ZSM-5 type zeolites. A suitable shape selective medium pore catalyst for fixed bed processes is an acidic H-ZSM-5 type ferrosilicate zeolite with alumina binder in the form of cylindrical extrudates or binder-free pellets. While the dominant framework metal is Fe, it is understood that minor amounts of other tetrahedrally coordinated metals may be incorporated in the zeolite structure, such as Al, Ga or B. Additional metals include optional Cr, V and Co species.

Catalyst A

A ferrosilicate zeolite having a ZSM-5 crystalline structure is prepared. A first solution containing 4.9 parts by weight of $Fe(NO_3)_3.9\ H_2O$, 6.6 parts $H_2SO_4$ (conc.) and 30.7 parts $H_2O$ is mixed with a second solution of 7 parts tetrapropylammonium bromide in 16.4 parts $H_2O$, to which is added 9.7 parts $Na_2SO_4.10\ H_2O$. Another solution is prepared by dissolving 21.9 parts by weight of acid extracted $SiO_2$ into 6.6 parts NaOH in 96.1 parts $H_2O$ and heating to 80° C. These materials are stirred in an autoclave for 10 minutes and 3/parts of $Na_2SO_4$. and 5 parts aq. 10N NaOH are added prior to heating the sealed autoclave at 165° C. for 6 days.

The ferrosilicate zeolite product is filtered, washed, and calcined in nitrogen at 540° C. for 10 hours. This zeolite contains 3.7 wt.% Fe and 180 ppm $Al_2O_3$. Following ammonium ion exchange and calcination, the hydrogen form of the catalyst is obtained. The structure is confirmed by x-ray diffraction, temperature-programmed ammonia sorption and infra-red spectroscopic studies. Mossbauer spectra indicate the presence of trivalent Fe and about 60 to 70% of Fe species are found tetrahedrally coordinated in the zeolite lattice structure as framework atoms. A characteristic IR band at 3630 cm$^{-1}$ is assigned to acidic OH groups associated with framework Fe. The Bronsted acid activity is found to be less than analogous aluminum ZSM-5 zeolites.

Suitable oligomerization catalyst is prepared from the above-synthesized ferrosilicate zeolite by dry forming in binder free pellets and screening to a 14×30 size.

Catalyst B

Silicate 1 is prepared according to the procedure of U.S. Pat. No. 4,238,318 (Kovwenhoven et al). This ferrosilicate zeolite contains 6.5 wt.% Fe and 860 ppm $Al_2O_3$. A minor amount of the iron is believed to be present in the zeolite framework.

Catalyst C

An aluminosilicate is prepared according to U.S. Pat. Re. 29,948 to provide an acidic ZSM-5 with 500 ppm $Al_2O_3$.

EXAMPLES 1-5

A series of standard experimental olefinic conversion runs is conducted using a standard fixed bed of pelletized zeolite catalyst under substantially isothermal conditions at 230° C. (446° F.) and 10400 kPa (1500 psig), using each of the above identified catalysts. The results are set forth in the Table below.

TABLE

| | EXAMPLE NO. | | | | |
|---|---|---|---|---|---|
| | 1 | 2 | 3 | 4 | 5 |
| | FeZSM-5 | FeZSM-5 | FeZSM-5 | FeZSM-5 | (Al)ZSM-5 |
| Catalyst = | A | B | A | A | C |
| Fe = | 3.7 wt. % | 6.5 | 3.7 | 3.7 | nil |
| $Al_2O_3$ = | 180 ppm | 860 | 180 | 180 | 500 |
| Feed = | propene | propene | butene-1 | butene-1 | butene-1 |
| Space Val. (LHSV) = | 0.38 | 0.38 | 0.33 | 0.33 | 0.33 |
| Time on Stream (Hrs.) = | 22 | 22 | 19 | 44 | 50 |
| Products (wt. %) | | | | | |
| $C_1-C_5$ | 1.1 | 76.8 | 3.4 | 2.2 | 93.4 |
| $C_6$-330° F. | 22.7 | 14.4 | 37.4 | 38.2 | 2.4 |
| 330-650° F. | 64.9 | 7.7 | 51.2 | 51.8 | 2.2 |
| 650° F.+ | 11.3 | 1.0 | 7.7 | 7.8 | 2.0 |

In the application of the present invention to industrial processes for olefins upgrading, conditions may be employed according to U.S. Pat. Nos. 4,150,062, 4,211,640, 4,227,992 (Garwood et al), 4,324,940 (Dessau), 4,433,185 (Tabak) and/or 4,456,770 (Owen et al), incorporated herein by reference. The process is particularly advantageous in the production of liquid hydrocarbons such as gasoline, diesel fuel and lubricants.

What is claimed is:

1. A process for upgrading lower olefin to produce heavier hydrocarbons having a substantially linear molecular conformation comprising:
   contacting olefinic feedstock under oligomerization conditions at reaction temperature and pressure favorable to formation of higher molecular weight aliphatic hydrocarbons with a shape selective medium pore acidic crystalline ferrosilicate zeolite catalyst having a major portion of zeolitic iron in tetrahedral coordination therein.

2. The process of claim 1 wherein $C_2-C_8$ olefinic feedstock is converted at a reaction temperature of about 175° to 375° C., a pressure of about 1000 to 20,000 kPa and space velocity of about 0.1-10 LHSV in the essential absence of hydrogen.

3. The process of claim 1 wherein the reaction temperature is about 230° to 270° C., olefin partial pressure is about 3500 to 15,000 kPa, and space velocity is less than 1 LHSV, and wherein the catalyst consists essentially of ZSM-5 type ferrosilicate.

4. The process of claim 1 wherein the feedstock comprises a major portion of $C_3-C_4$ olefin.

5. The process of claim 1 wherein the catalyst consists essentially of ferrosilicate having a constraint index of about 1 to 12 and having at least about 60% of Fe tetrahedrally coordinated in the zeolite lattice.

6. The process of claim 1 wherein the heavy hydrocarbon product comprises a major portion of distillate range hydrocarbons.

7. A process for oligomerizing lower olefin to heavier hydrocarbons comprising
   contacting olefinic feedstock under oligomerization conditions at reaction temperature of about 175° to 375° C. and olefin particle pressure of about 3500 to 15,000 kPa with a shape selective medium pore acidic crystalline ferrosilicate ZSM-5 type zeolite catalyst having a major portion of zeolitic iron in tetrahedral coordination therein.

8. The process of claim 7 wherein the ferrosilicate zeolite contains at least about 3.7 weigth percent Fe having at least about 60% framework Fe.

* * * * *